US009734706B2

(12) United States Patent
Moon et al.

(10) Patent No.: US 9,734,706 B2
(45) Date of Patent: Aug. 15, 2017

(54) MULTIFUNCTION CABLE FOR USE WITH DIFFERENT SIGNAL INPUTS

(71) Applicant: Clinical Innovations, LLC, Murray, UT (US)

(72) Inventors: Brandon D. Moon, Highland, UT (US); Kristian J. Olsen, Saratoga Springs, UT (US); Jeremy C. Horton, Salt Lake City, UT (US)

(73) Assignee: Clinical Innovations, LLC, Murray, UT (US)

( * ) Notice: Subject to any disclaimer, the term of this patent is extended or adjusted under 35 U.S.C. 154(b) by 319 days.

(21) Appl. No.: 13/830,239

(22) Filed: Mar. 14, 2013

(65) Prior Publication Data
US 2014/0266775 A1   Sep. 18, 2014

(51) Int. Cl.
*G08C 19/32*   (2006.01)
*A61B 5/03*    (2006.01)
(Continued)

(52) U.S. Cl.
CPC .............. *G08C 19/32* (2013.01); *A61B 5/033* (2013.01); *A61B 5/035* (2013.01); *A61B 5/4343* (2013.01);
(Continued)

(58) Field of Classification Search
CPC .......... G06F 3/0416; G09G 2310/0297; G09G 2300/0426
See application file for complete search history.

(56) References Cited

U.S. PATENT DOCUMENTS 4,567,763 A * 2/1986 Schiffbauer .................. 73/866.1
5,263,485 A * 11/1993 Hickey .......................... 600/486
(Continued)

FOREIGN PATENT DOCUMENTS

JP   2008246094 A   10/2008
WO   2012108950     8/2012

OTHER PUBLICATIONS

Clinical Innovations, "Koala. Your Complete Tool to Systematically Eliminate IUP Inaccuracies", Koala Features Brochure, 2 pages, © 2005 Clinical Innovations, Inc.
(Continued)

*Primary Examiner* — Hai Phan
*Assistant Examiner* — Son M Tang
(74) *Attorney, Agent, or Firm* — TraskBritt (57) ABSTRACT

A cable comprises a circuit, a switching element and an input connection for engaging an output connection of a sensor, the switching element configured to selectively enable the circuit of the cable assembly to process an accepted output of at least one of at least two sensors providing differing acceptable outputs and to provide a signal output corresponding to the accepted sensor output for processing by a monitor. A sensor includes an initiation element structured to cause a switching element associated with an input connection of the cable to change a mode of operation of the switching element to selectively enable the circuit to process an output of the sensor accepted by the cable and to provide a signal output corresponding to the accepted sensor output. A system comprises a monitor and the cable including the circuit and the switching element. Methods of operation are also disclosed.

15 Claims, 8 Drawing Sheets

(51) Int. Cl.
*A61B 5/00* (2006.01)
*A61B 5/20* (2006.01)
*A61M 39/10* (2006.01)

(52) U.S. Cl.
CPC .............. *A61B 5/037* (2013.01); *A61B 5/20* (2013.01); *A61B 5/4255* (2013.01); *A61B 5/6852* (2013.01); *A61B 5/7225* (2013.01); *A61B 2562/222* (2013.01); *A61B 2562/224* (2013.01); *A61B 2562/226* (2013.01); *A61B 2562/227* (2013.01); *A61M 2039/1077* (2013.01); *G08C 2201/30* (2013.01)

(56) References Cited

U.S. PATENT DOCUMENTS

| | | | | |
|---|---|---|---|---|
| 5,330,521 | A * | 7/1994 | Cohen | 607/122 |
| 5,573,007 | A * | 11/1996 | Bobo, Sr. | 600/561 |
| 5,951,497 | A * | 9/1999 | Wallace et al. | 600/587 |
| 5,984,879 | A * | 11/1999 | Wallace et al. | 600/587 |
| 5,995,855 | A * | 11/1999 | Kiani | A61B 5/14551 600/310 |
| 6,231,524 | B1 | 5/2001 | Wallace et al. | |
| 6,259,938 | B1 * | 7/2001 | Zarychta et al. | 600/380 |
| 6,447,462 | B1 | 9/2002 | Wallace et al. | |
| 8,118,620 | B2 * | 2/2012 | Al-Ali | H01R 13/6275 439/607.27 |
| 8,315,683 | B2 * | 11/2012 | Al-Ali | A61B 5/14552 600/310 |
| 8,386,000 | B2 * | 2/2013 | McKenna | A61B 5/14551 600/310 |
| 2005/0037661 | A1 * | 2/2005 | Tanacan et al. | 439/488 |
| 2005/0171437 | A1 * | 8/2005 | Carberry | 600/476 |
| 2005/0187440 | A1 | 8/2005 | Abdul-Hafiz | |
| 2006/0285637 | A1 | 12/2006 | Varjonen et al. | |
| 2008/0082024 | A1 | 4/2008 | Meyer et al. | |
| 2009/0247852 | A1 | 10/2009 | Boyce et al. | |
| 2009/0273496 | A1 * | 11/2009 | Renner | 341/119 |
| 2011/0077473 | A1 | 3/2011 | Lisogurski | |
| 2011/0112440 | A1 | 5/2011 | Euliano, II et al. | |
| 2012/0130239 | A1 | 5/2012 | Meyer et al. | |

OTHER PUBLICATIONS

International Search Report and Written Opinion for PCT application PCT/US2014/024369, dated Aug. 18, 2014, 11 pages.
International Preliminary Report on Patentability for PCT application PCT/US2014/024369, dated Sep. 15, 2015.
Extended European Search Report for EU Application No. 14774209.2 dated Nov. 16, 2016, 10 pages.

* cited by examiner

FIG. 8

MULTIFUNCTION CABLE FOR USE WITH DIFFERENT SIGNAL INPUTS

TECHNICAL FIELD

Embodiments of the present disclosure relate to connections between sensors providing differing outputs and monitors configured to receive, process, and display information corresponding to each of the differing outputs. More particularly, embodiments of the present disclosure relate to a multifunction cable configured to receive differing inputs from sensors and determine which of the differing inputs is present and convert the determined input to a signal usable by the monitor.

BACKGROUND

Physical parameters exhibited by a woman in labor in the form of uterine contractions are conventionally monitored using a sensor in the form of a tocodynamometer (hereinafter a "toco"), an intrauterine pressure catheter (hereinafter an "IUPC"), or both types of sensors. Ideally, it is desirable to monitor amplitude, frequency and duration of contractions prior to delivery of an infant. Other physical parameters are also monitored using other types of sensors.

Conventional tocos employ a strain gauge mechanism supported within a rigid ring, termed a "guard ring." Such tocos exhibit very low compliance (e.g., deflection) when the force of a uterine contraction is applied, cannot provide data on contraction intensity, and are susceptible to artifact when employed with certain patient physiologies such as patients with substantial belly fat, or a thin uterus. Further, such conventional tocos are heavy, nondisposable and costly to purchase, on the order of $300 to $500 each, costly to repair, and are specific to a particular manufacture of monitor. In addition, even with proper cleaning procedures, such tocos may present a risk of cross-contamination between patients.

Recently, a low-cost, lightweight, disposable so-called "pneumatic" toco has been developed, which pneumatic toco assertedly equals if not improves the performance of a conventional guard-ring, strain gauge toco. The pneumatic toco, at a cost of under ten dollars ($10), generates an output in the form of pressure differences within a closed interior air volume as varied by uterine contractions acting upon an elastic membrane and as sensed and converted to electrical signals by a pressure transducer at the distal end of a reusable cable in communication with the closed air volume. Such a pneumatic toco and its operation are described in International PCT Publication No. WO 2012/108950, published Aug. 16, 2012, as applied for by the Board of Trustees of the University of Arkansas on behalf of inventors Hari Eswaran, Curtis L. Lowry and James D. Wilson, the disclosure of which publication is hereby incorporated herein in its entirety by this reference.

A highly commercially successful, low cost, disposable intrauterine pressure catheter has been developed and marketed by Clinical Innovations, LLC, of Murray, Utah as the KOALA® intrauterine pressure catheter (IUPC). The KOALA® IUPC employs a closed air volume to measure frequency, duration and intensity of uterine contractions via a pressure transducer at the distal end of a reusable cable assembly sensing pressure differences in the closed air volume. The KOALA® IUPC and its operation are described in U.S. Pat. Nos. 5,951,497; 5,984,879 and 6,231,524, all assigned to the assignee of the present disclosure and the disclosure of each of which patents is incorporated herein in its entirety by this reference. The commercial success of the KOALA® IUPC has been of such magnitude that it is employed in virtually every hospital throughout the United States, as well as enjoying substantial use in Europe.

Other sensing devices using a closed air volume include LATITUDE® esophageal catheters and anorectal catheters, developed and marketed by Clinical Innovations, LLC, of Murray, Utah.

Urodynamic catheters employing a closed air volume are commercially available as T-DOC® air-charged catheters from T-DOC Company, LLC of Wilmington, Del. Pressure differences within the closed air volume are sensed by a pressure transducer at the distal end of a reusable cable. The T-DOC® catheter and its operation are described in U.S. Pat. No. 6,447,462, assigned to the assignee of the present disclosure, the disclosure of which patent is incorporated herein in its entirety by this reference.

It would be desirable, as recognized by the inventors herein, to be able to employ a single, reusable cable to provide input from different disposable sensors to a monitor. However, sensors such as closed air volume sensors, which employ no electrical circuitry in the sensor itself, present challenges in development of a multi-use cable.

BRIEF SUMMARY

In one embodiment of the present disclosure, a cable assembly comprises a circuit, a switching element and an input connection for engaging an output connection of a sensor, the circuit of the cable assembly configured to accept different outputs of at least two different sensors having a common output connection configuration and to provide a signal corresponding to the accepted sensor output, and the switching element configured to selectively enable the circuit to process the accepted output of at least one of the at least two different sensors prior to providing the signal corresponding thereto.

In another embodiment, a sensor comprises a sensor element, an output connection in communication with the sensor element and an initiation element proximate the output connection, and structured to cause a switching element associated with cooperative input connection of a cable comprising a circuit to change a mode of operation of the switching element responsive to engagement of the output connection with the input connection to enable the circuit of the cable to process an electrical signal corresponding to an output of the sensor element and to provide a processed electrical signal corresponding to the output.

In yet another embodiment, a system comprises a monitor, a cable including a circuit, an input connection for engaging an output connection of a sensor, and a switching element associated with the input connection, the switching element configured to selectively enable the circuit of the cable to process an output of at least one of at least two different sensors configured to provide differing outputs accepted by the circuit and to provide a signal output corresponding to the accepted sensor output to the monitor.

In a further embodiment, a method of using sensors comprises connecting a sensor configured to provide an output to a cable operably coupled to a monitor, providing the sensor output to the cable, converting the sensor output to corresponding electrical signals usable by the monitor and transmitting the electrical signals corresponding to the sensor output through the cable to the monitor, disconnecting the sensor from the cable, connecting to the cable another sensor configured to provide a different output from the output of the sensor, providing the different sensor output to the cable, converting the different sensor output to corresponding different electrical signals, processing the different electrical signals into a form usable by the monitor, and transmitting the processed different electrical signals to the monitor.

DETAILED DESCRIPTION

The illustrations presented herein are not actual views of any particular sensor device or multifunction cable, but are merely idealized representations which are employed to describe embodiments of the present disclosure.

As used herein, the terms "cable" and "cable assembly" mean and include without limitation any device or apparatus configured with a circuit for accepting an output of a sensor, processing the output and providing a signal for use by a monitor comprising a processor and optionally a display, and is not limited to a conventional, elongated cable structure or any other particular physical configuration. In some embodiments, the cable may comprise a connector comprising a housing including the circuit and configured connection to a sensor output and for direct connection to a monitor.

As used herein, the term "process," when in reference to an electrical signal, means and includes altering characteristics of the electrical signal to enable use thereof by a receiving apparatus such as, for example, a monitor comprising a processor and, optionally, a display. One nonlimiting example of processing of an electrical signal is amplification of the signal.

Figure 1:
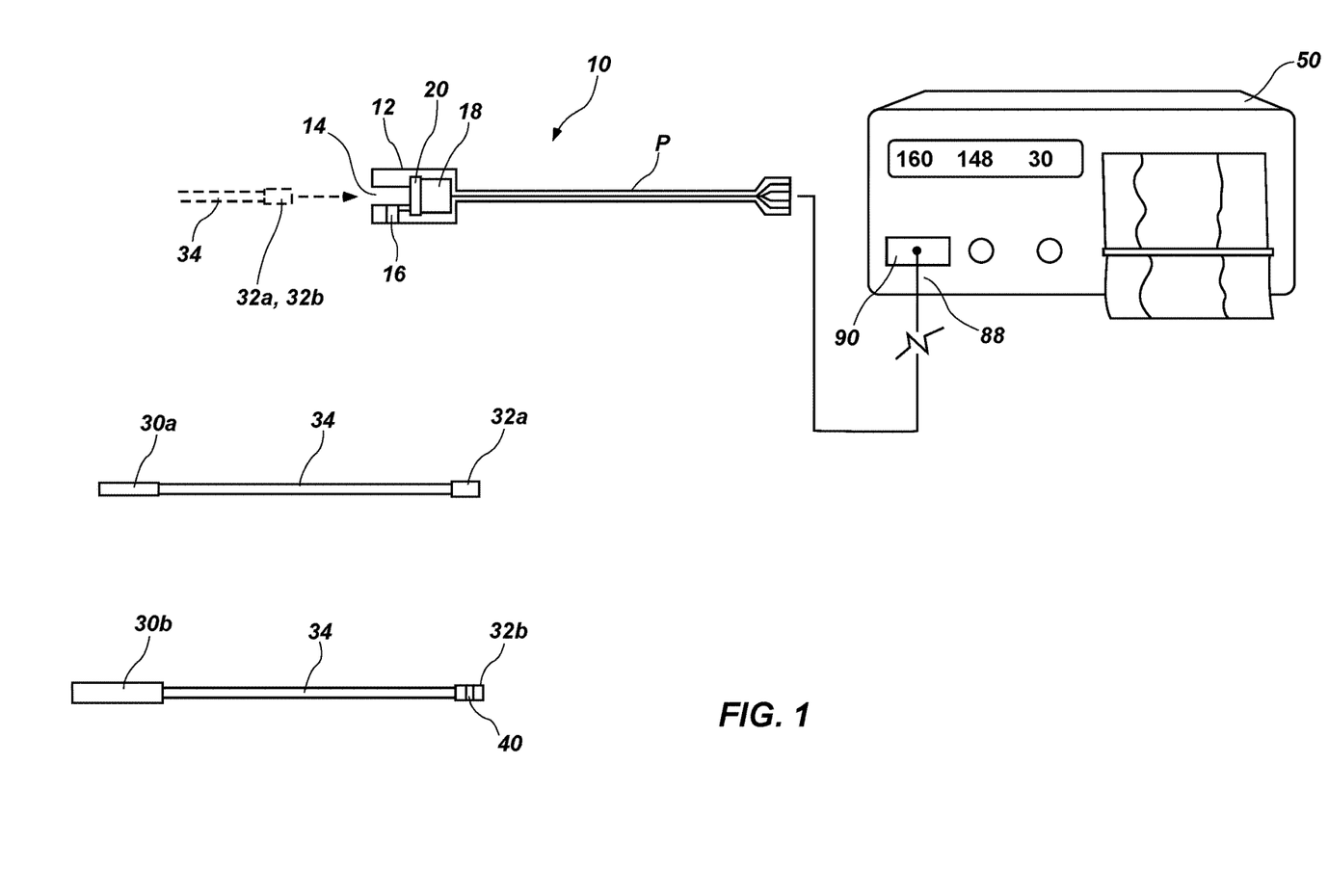
FIG. 1 is a schematic of an embodiment of a cable according to the present disclosure, a monitor connected to the cable and two sensors having different outputs and configured to operably couple with the cable.

In some embodiments and with reference to FIG. 1, a cable assembly 10 comprises an input housing 12 including an input connection in the form of input receptacle 14, a switching element 16 having at least two modes of operation proximate the input receptacle 14, and a circuit 18 operably coupled to switching element 16 and configured for converting a sensor output to an electrical signal usable by a monitor 50 (e.g., a monitor configured to monitor uterine contractions) to which cable assembly 10 is operably coupled, either directly or through an elongated multiconductor path P as depicted. A proximal end 88 of the cable assembly 10 may include an electrical connector 90 for attachment to the monitor 50. Input receptacle 14 is configured to accept an output connection in the form of male connector 32a of a sensor 30a, male output connector 32a being in communication with sensor 30a through a length of tubing 34. In one embodiment, output of sensor 30a comprises differences in pressure within a closed air volume contained within sensor 30a and tubing 34 when male output connector 32a is engaged with input receptacle 14 of input housing 12.

In such an embodiment, circuit 18 comprises a pressure transducer 20 in communication with input receptacle 14 for sensing pressure differences within the closed air volume, and circuit 18 further comprises components (e.g., the circuit 150 of FIG. 7 or the circuit 150A of FIG. 8, both described in detail below) for processing an electrical signal from pressure transducer 20 corresponding to pressure differences detected by at least one of sensor 30a and another sensor 30b, each providing a different pressure output, into an electrical signal usable by monitor 50. Stated another way, circuit 18 may not process an electrical signal from pressure transducer 20 corresponding to an output from one of sensors 30a and 30b if such signal is suitable to merely be passed on to a monitor, but may process an electrical signal from the other of sensors 30a and 30b to render the signal suitable for use by the monitor. Alternatively, circuit 18 may be configured to process electrical signals from pressure transducer 20 corresponding to outputs of both sensor 30a and sensor 30b, but process the signals differently responsive to a mode of switching element 16. By way of example and not limitation, circuit 18 may be configured to amplify an output of sensor 30a at a first gain, and to amplify an output of sensor 30b at a second, different gain. The sensor 30b is also configured with and communicates sensed pressures to a male output connector 32b configured for engagement with input receptacle 14 through a length of tubing 34. Input receptacle 14 is configured to accept both male output connector 32a and male output connector 32b interchangeably.

An output of sensor 30b, like that of sensor 30a, comprises differences in pressure within a closed air volume, but as noted the output of sensor 30b differs (for example, in relative magnitudes) from the output of sensor 30a and, so may require processing by circuit 18 or different processing than processing employed with sensor 30a, to provide an electrical output signal from cable assembly 10 corresponding to the output of sensor 30b and usable by a common monitor. Male output connector 32b may include an initiation element 40 which, when male output connector 32b is inserted in receptacle 14, is in operable cooperative proximity to switching element 16 to cause switching element 16 to transition from a first mode to a second mode and enable circuit 18 to convert the electrical signals from pressure transducer 20 corresponding to pressures detected by sensor 30b to appropriate electrical signals usable by the monitor.

Although the cable assembly 10 has been described as including a female input receptacle 14 and the sensors 30a and 30b have been described as including male output connectors 32a and 32b, the present disclosure is not so limited. For example, in some embodiments, the input receptacle 14 may be a male connector and the output connectors 32a and 32b may be female connectors.

Switching element 16 and cooperative initiation element 40 may take a number of forms, in various embodiments of the present disclosure. Example embodiments of the switching element 16 and cooperative initiation element 40 are shown in FIGS. 2A through 2E.

Figure 2A:
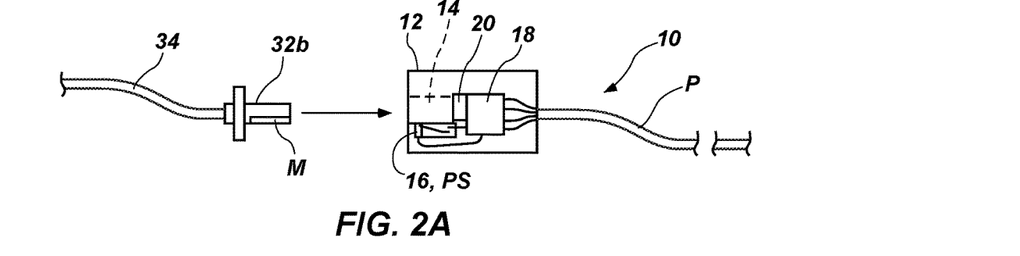
FIGS. 2A through 2E are, respectively schematics of different switching mechanisms comprising switching elements and cooperative initiation elements according to the present disclosure and suitable for use with the cable and sensors.

In one embodiment, as depicted in FIG. 2A, switching element 16 may comprise a proximity switch PS such as a reed switch or a Hall effect sensor, and initiation element 40 may comprise a magnet or other metal M suitable for cooperatively interacting with proximity switch PS secured to male output connector 32b of sensor 30b and positioned, when male output connector 32b is received in receptacle 14, to cause proximity switch PS to transition from a first mode to a second mode, completing or opening a circuit and enabling circuit 18 to function in a mode operable to process the output of sensor 30b as converted to electrical signals by pressure transducer 20 rather than in a mode to process the converted output of sensor 30a, or to enable circuit 18 to process the converted output of sensor 30b, circuit 18 in the previous mode passing through signals from pressure transducer 20 without processing.

Figure 2B:
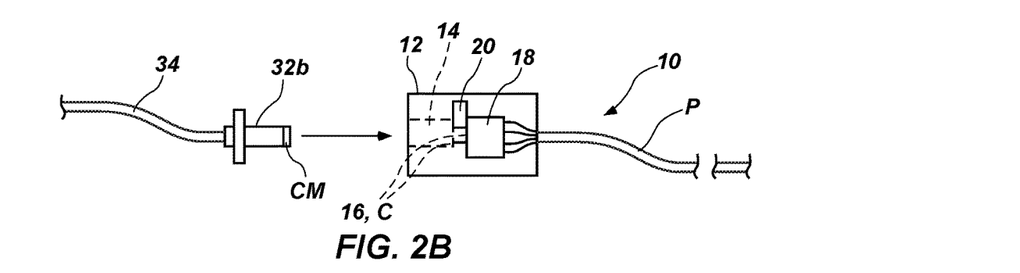

In another embodiment, as depicted in FIG. 2B, switching element 16 may comprise two spaced contacts C in the form of conductive pins (fixed or biased) or pads, and initiation element 40 may comprise an element of metal or other conductive material CM which completes a circuit path between spaced contacts C when male output connector 32b is received in receptacle 14 and enables circuit 18 to function in a mode operable to process the output of sensor 30b as converted to electrical signals by pressure transducer 20 rather than in a mode to process the converted output of sensor 30a, or to enable circuit 18 to process the converted output of sensor 30b, circuit 18 in the previous mode passing through signals from pressure transducer 20 without processing.

Figure 2C:
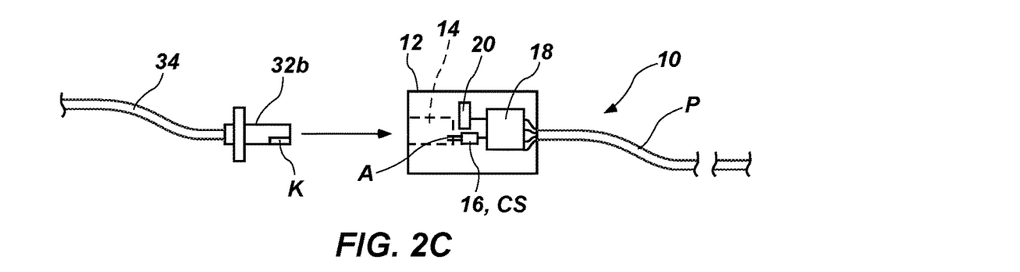

In another embodiment, as depicted in FIG. 2C, switching element 16 may comprise a spring-biased contact switch CS and initiation element 40 may comprise key element K which may ensure rotational orientation of male output connector 32b with respect to an actuation A element on contact switch CS and engages (e.g., presses) actuation element A to either complete a circuit (if contact switch CS is a normally open, or "n.o.," switch) or open a circuit (if contact switch CS is a normally closed, or "n.c.," switch) when male output connector 32b is received in receptacle 14 and enable circuit 18 to function in a mode operable to process the output of sensor 30b as converted to electrical signals by pressure transducer 20 rather than in a mode to process the converted output of sensor 30a, or to enable circuit 18 to process the converted output of sensor 30b, circuit 18 in the previous mode passing through signals from pressure transducer 20 without processing.

Figure 2D:
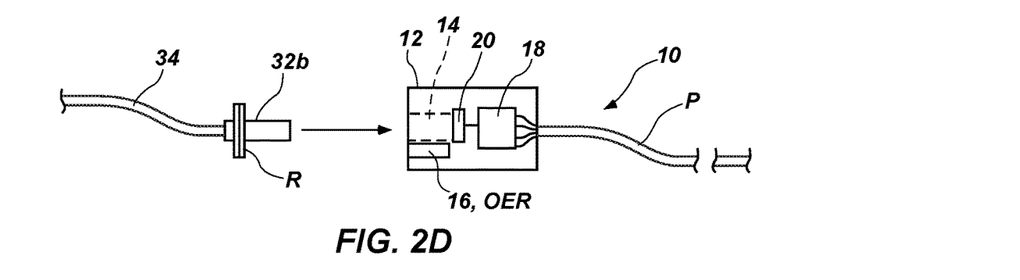

In a further embodiment, as depicted in FIG. 2D, switching element 16 may comprise an optical emitter/receiver switch (OER switch) and initiation element 40 may comprise a reflective element R which reflects an emitted light signal (for example, visible or infrared) from the optical emitter when male output connector 32b is received in receptacle 14 to the optical receiver to cause the OER switch to either complete a circuit or open a circuit when male output connector 32b is received in receptacle 14 and enable circuit 18 to function in a mode operable to process the output of sensor 30b as converted to electrical signals by pressure transducer 20 rather than in a mode to process the converted output of sensor 30a, or to enable circuit 18 to process the converted output of sensor 30b, circuit 18 in the previous mode passing through signals from pressure transducer 20 without processing. In some embodiments, the reflective element R may be replaced by a light conductive material, such as a fiber optic material, that functions similarly to the reflective element R described above in that the light conductive material interacts with an optical emitter to switch between an opened and a closed state.

Figure 2E:
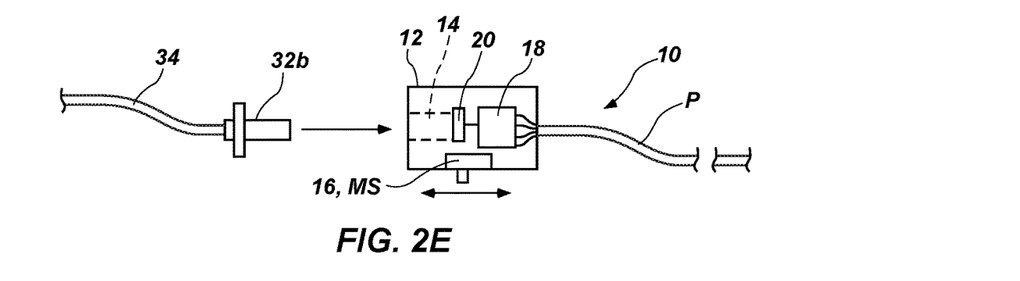

In yet another embodiment, as depicted in FIG. 2E, switching element 16 may comprise a manually operated contact switch MS accessible from the exterior of housing 12, and an operator's hand may be used to manipulate contact switch MS from one mode to another to enable circuit 18 to process the output of either sensor 30a or sensor 30b as measured by pressure transducer 20.

Figure 3:
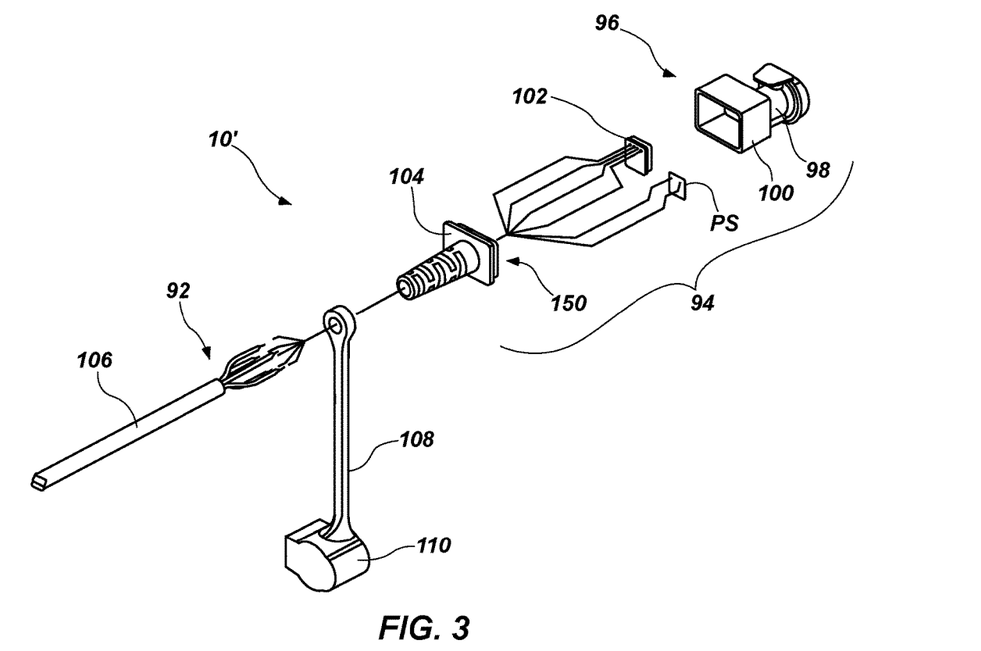
FIG. 3 comprises an exploded perspective view of an input portion of a cable comprising an input connection and selected circuitry according to an embodiment of the disclosure.
Figure 4A:
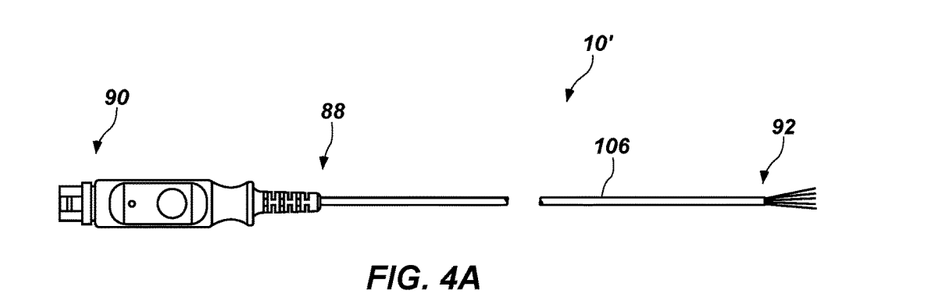
FIGS. 4A and 4B comprise, respectively, a side elevation and a side elevation rotated 90° about a cable axis of an output section of the cable of FIG. 3.
Figure 4B:
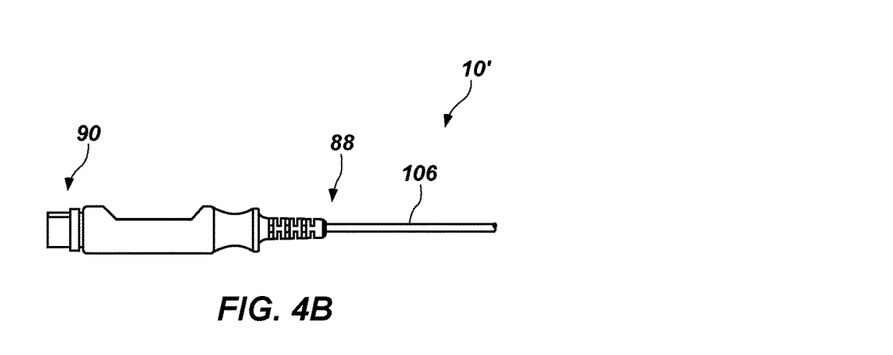
Figure 5:
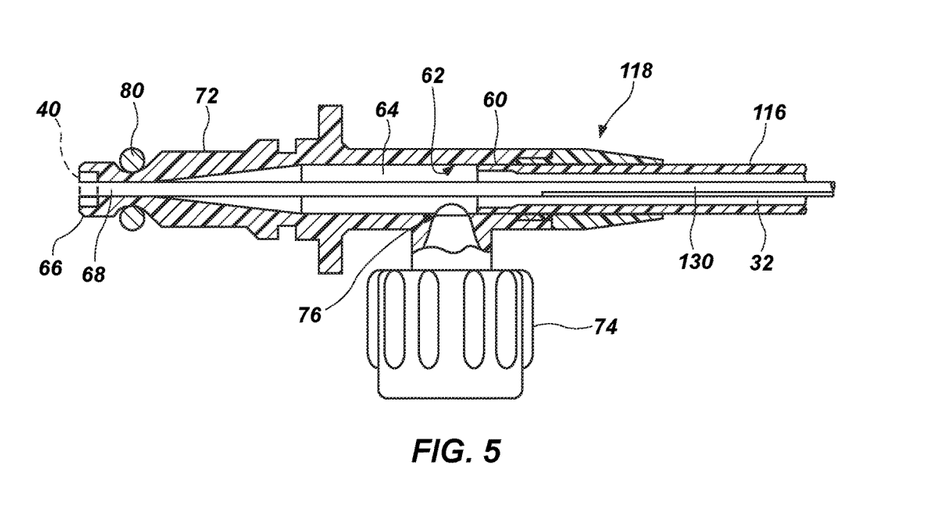
FIG. 5 comprises a side sectional elevation of an embodiment of an output connection for a sensor, the output connection configured to engage the input connection of FIG. 3.

FIG. 3 depicts an input portion of a reusable cable assembly 10' comprising an input connection and selected circuitry according to an embodiment of the disclosure, input portion of cable assembly 10' being physically similar to the input portion of cable assembly illustrated in FIG. 5 of U.S. Pat. No. 5,984,879 ("the '879 patent"), previously incorporated herein by reference. FIGS. 4A and 4B depict an output portion of reusable cable assembly 10'. An IUP catheter as described in the '879 patent and identified in FIG. 1 thereof as reference numeral 10 and identified in FIG. 5A of the present application as IUPC comprising a sensor in the form of balloon B and male output connector 72, is configured to be detachably attached to reusable cable assembly 10', which is structured to be plugged into a fetal monitor, which may comprise monitor 50 as illustrated in FIG. 1. The reusable cable assembly 10' has, at its proximal end 88, an electrical connector 90 (FIGS. 4A and 4B), which is sized and configured for attachment to a fetal monitor. At the distal end 92 of the cable assembly 10' is a pressure detection and signal conversion assembly 94 which interfaces with an air column of the IUPC to detect changes in intrauterine pressure. The pressure detection and signal conversion assembly 94 may, as shown in FIGS. 3 and 6 of the drawings of the present application, comprise a coupling 96 structured with a female input connector 98 sized to receive a male output connector 72 of the IUPC (FIG. 5A) (or the male output connector 32a or 32b of the sensor 30a or 30b (FIG. 1)), an enclosure 100 for retaining a pressure sensor 102 and an end cap 104 for capping the enclosure 100 and attaching the pressure detection and signal conversion assembly 94 to a tubular cable 106 of the reusable cable assembly 10'. A circuit 150 may be electrically coupled to the pressure sensor 102 and configured to process an electrical signal from the pressure sensor 102 depending on the type of sensor coupled to the pressure detection and signal conversion assembly 94. A protective cover 108 may also be provided on the reusable cable assembly 10' and have a cap 110 sized to fit over the exposed end of the female input connector 98 when the reusable cable assembly 10' is not connected to the IUPC.

Figure 5A:
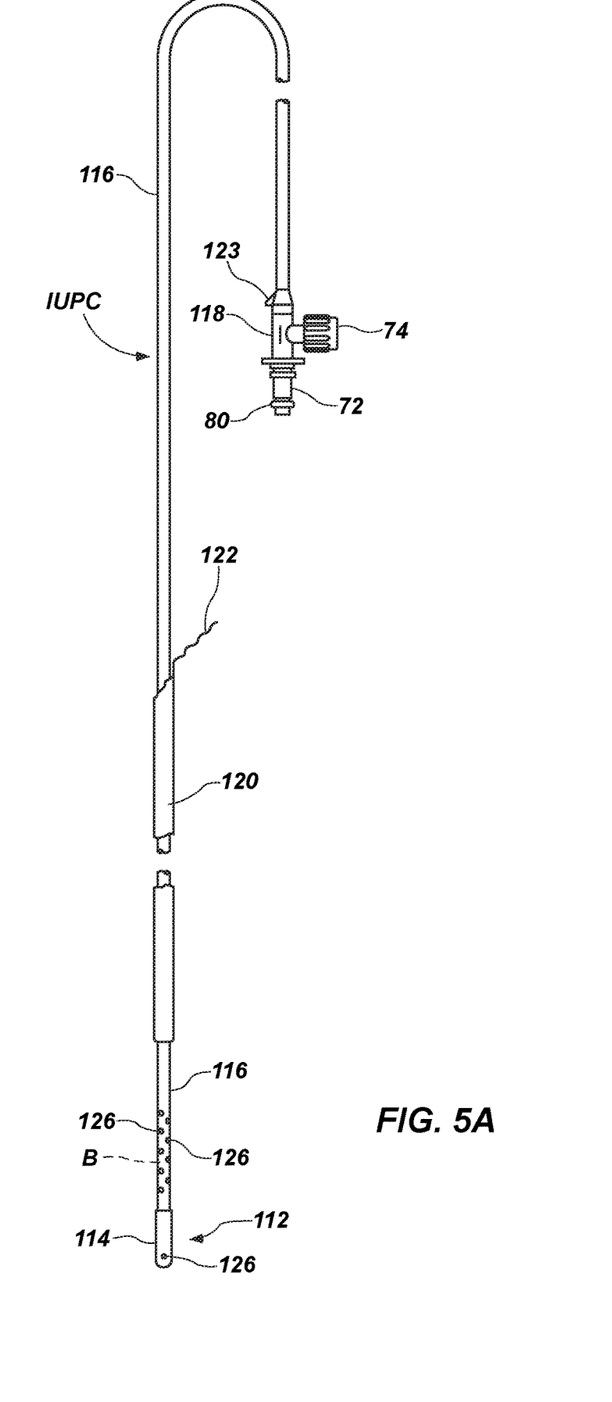
FIG. 5A is a side elevation of a sensor configured for use with an embodiment of the present disclosure when employed with an output connection as depicted in FIG. 5.
Figure 6:
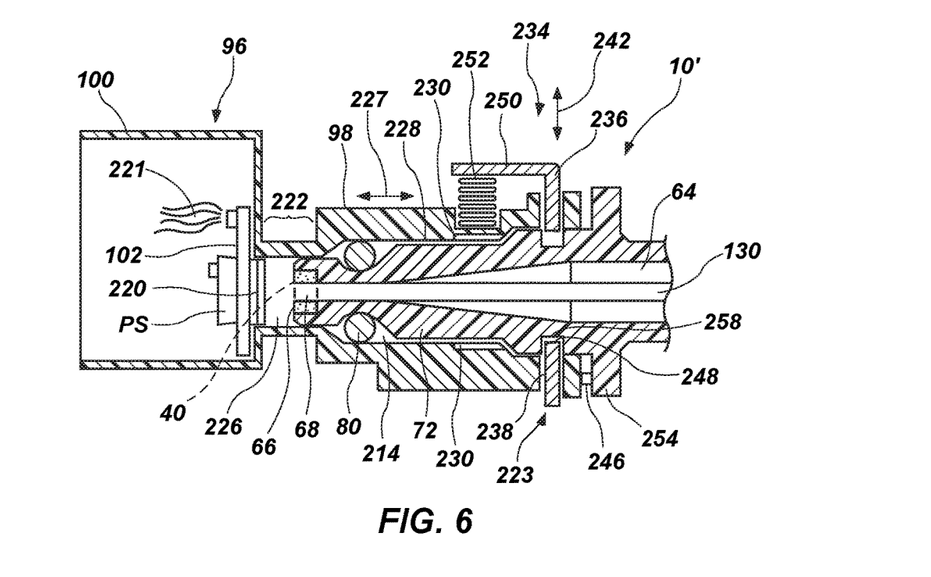
FIG. 6 comprises a side sectional view of the output connection of FIG. 5 engaged with the input connection of FIG. 3.

FIG. 5A illustrates an embodiment of a disposable intrauterine pressure catheter IUPC configured for use with reusable cable assembly 10'. At the distal end 112 of the IUPC there is formed a soft, pliant tip 114, which facilitates insertion of the IUPC into the uterus. The soft tip 114 may be formed of a material that is pliant enough to deflect or give as the tip 114 encounters a resistive force, such as the fetus, placenta or the uterine wall. A low durometer plastic or elastomer such as polyvinyl chloride (PVC) or a polyurethane is highly suitable. The tip 114 is attached to an elongated outer hollow tube 116, which extends from the tip 114 at its distal end to a housing 118 at its proximal end. The outer hollow tube 116 is formed of flexible, biocompatible material such as PVC or a polyolefin, with sufficient wall thickness to resist collapse under normal conditions, and sized in length to extend from within the uterus of a patient to outside the body of the patient. Thus, for example, the outer hollow tube may range in length from 60 cm to 90 cm. A tear-away sheath 120 may be initially positioned about the outer hollow tube 116 to facilitate insertion of the IUPC into the uterus. After insertion of the IUPC the tear-away sheath 120 is removed, such as by pulling on thumb tab 122 and slitting against a ramp or other protrusion 123 at the proximal end of the IUPC. A plurality of holes 126 is formed through the wall of the outer hollow tube 116 immediately behind the tip 114. The pattern of holes 126 may vary, but, preferably, the holes 126 are distributed about the circumference of the outer hollow tube 116 and longitudinally therealong to allow fluid to enter into the outer hollow tube 116 from any direction thereabout. A plurality of holes 126 is provided so that, if any one or more holes 126 should become clogged with matter from the amniotic fluid, other holes 126 will be available for allowing passage of fluid, and transmission of fluid pressure, therethrough. The holes 126 extend for a distance beyond the tip 114 in the direction of the proximal end of the outer hollow tube 116. The holes 126 may extend anywhere from one millimeter to several centimeters beyond the tip 114. One or more holes 126 may also be formed through the tip 114. In an alternative embodiment, slits may be formed through the wall of the outer hollow tube 116. The holes or slits may extend proximally of the most proximal end of a balloon B disposed within tube 116 so that excessive infusion of fluid entering tube 116 will not disturb the balloon and induce artifact into the pressure signal generated thereby.

Referring to FIG. 5 in conjunction with FIG. 5A, air or another gas may occupy the interior of the inner tube 130 and is at atmospheric pressure prior to use of the IUPC. The inner tube 130 and the balloon B attached to the inner tube 130 may, therefore, form or define an air column that may extend from the housing 118 to near the tip 114 of the IUPC. When the IUPC is attached to a cable assembly 10', as explained further below, the air column becomes filled, or "charged," with an additional quantity of air. The additional air charged into the air column fills the balloon B, at least partially, to a selected volume. The material of the balloon B is very pliant due to its thin wall and the low durometer material used in its construction, and the balloon B deforms easily, and substantially without artifact introduced by the material of the balloon itself, with a given change in pressure external to the balloon B. The material of the balloon B may, for example, be about a 30 A Shore durometer hardness. A particularly suitable material for use in forming the inner tube 130 may be C-FLEX® synthetic elastomer (commercially available from Consolidated Polymer Technologies, Inc., Largo, Fla.) of 0.001-0.002 in. (1-2 mm) wall thickness, or any other similar material having similar durability and flexibility. Regardless of the material employed, less than 5 mm Hg of external pressure maximum should be required to collapse balloon B when its interior is vented to atmospheric pressure. The uterus typically has a 5-30 mm Hg resting tone, and therefore will ensure collapse of balloon B upon insertion of the IUPC and before charging. The collapse of balloon B before charging the air column, as subsequently described, provides an accurate pressure signal.

As shown in FIGS. 5 and 5A, in one embodiment of the IUPC as illustrated in FIG. 5A, the outer hollow tube 116 and the inner tube 130 are attached to a housing 118 in sealing engagement therewith. The proximal end 60 of the outer hollow tube 116 is attached to the inner surface 62 of the housing 18. The inner tube 130, which extends through the outer hollow tube 116, enters through the interior lumen 64 of the housing 118 and extends to the proximal extremity 66 of the housing 118. The proximal end 68 of the inner tube 130 is sealed to the proximal extremity 66 of the housing 118 by any suitable technique, such as by a sealing gasket and/or adhesive. The proximal end 68 of the inner tube 130 remains open. In the embodiment of the device illustrated in FIGS. 5 and 6, the housing 118 is structured with a male output connector 72 which is sized to be inserted into a female input connector 98 of a reusable cable assembly 10' as described more fully hereinafter. The male output connector 72 of the IUPC includes an O-ring or other annular seal element 80, which facilitates an air-tight seal between the IUPC and female input connector 98 of the reusable cable assembly 10' (FIG. 6). The housing 118 may also be formed with an amnio port 74 having an opening 76 that communicates with the interior lumen 64 of the housing 118. The interior lumen 64 is contiguous with the space 32 formed between the inner tube 130 and the outer hollow tube 116. Therefore, fluid entering the space 32 from the amniotic environment may be sampled or withdrawn from the amnio port 74. Alternatively, fluid may be injected into the uterine environment through the amnio port 74. In particular, a bolus of fluid can be injected into the amnio port 74 to flush the holes 126 formed near the tip 114 of the IUPC to dislodge any matter which may be occluding the holes 126. The IUPC as thus far described is detachably attachable to a reusable cable assembly 10' which is structured to be plugged into a monitor, such as the monitor 50 (FIG. 1).

As shown more clearly in FIG. 6, the female input connector 98 of reusable cable assembly 10' is attached to, or integrally formed with, the enclosure 100. The female input connector 98 has an internal bore or cavity 214 which is sized in internal diameter and length to snugly receive the male output connector 72 of the IUPC. Upon insertion of the male output connector 72 in the bore 214 of the female input connector 98, the O-ring 80 becomes seated against an inner wall 228 of the internal bore 214 to form an air-tight fit. Further, the proximal extremity 66 of the housing 118 and the open proximal end 68 of the inner tube 130 are positioned in close proximity to the pressure sensor 102 retained within the enclosure 100, minimizing dead space in the system. The pressure sensor 102 may be a pressure transducer, such as an NPC-109 manufactured by Lucas NovaSensors of Fremont, Calif., having a deformable diaphragm 220 which is positioned toward the female input connector means 98. Wiring 221 extends from the pressure sensor 102, through the enclosure 100, to a circuit 150, and to the proximal end 88 of the cable 106 (FIGS. 3 and 4A) for communication to a monitor. The bore 214 and throat 222 lying between the mouth 223 of the female input connector 98 and the enclosure 100 of the coupling 96 define an internal space 226 which contains a predetermined or selected volume of air prior to insertion of the male output connector 72 into the bore 214 of female input connector 98.

Thus, as the male output connector 72 is inserted like a piston or plunger into the bore 214 of female input connector 98 in the direction of arrow 227, part of the volume of air contained within the internal space 226 of the bore 214 is displaced by male output connector 72. The displaced volume of air is sufficient to "charge" or fill the balloon B of the IUPC (FIG. 5A) with an appropriate amount of air to expand the balloon B to function with desired sensitivity, responsive to a given range of pressure values, as more fully described in the '879 patent. As the male output connector 72 is inserted into the female input connector 98 and the O-ring 80 registers against the inner wall 228 surrounding the internal bore 214, excess air is released from the internal bore 214 through indented flutes 230 formed in the inner wall 228 so that the pre-charge volume of air is precisely defined. Stated another way, the effective air volume trapped in the air column is defined by the inward stroke or travel of male output connector 72 from the point at which O-ring 80 passes flutes 230 until male output connector 72 is fully inserted in female input connector 98. The female input connector 98 of the coupling 96 may be structured with a locking device 234 for retaining the male output connector 72 in the desired position within the female input connector 98.

As shown in FIG. 6, an example of a locking device 234 may comprise a slidable ring 236 which is positioned against, and slides within, a groove 238 formed in an outer flange 254 of the female input connector 98. The slidable ring 236 moves in the direction of arrow 242. A detent 246 engages a lip 248 of the slidable ring 236 when the locking device is in an unlocked position and thumb tab 250 is depressed against spring 252. As the male output connector 72 is inserted into the female input connector 98, the outer flange 254 of the male output connector 72 depresses the detent 246, disengaging the slidable ring 236 from its engagement with detent 246, and the spring 252, pushing against the thumb tab 250, moves the slidable ring 236 laterally. The lip 248 of the slidable ring 236 is urged into a groove 258 formed in the male output connector 72 and locks the male output connector 72 in place. The male output connector 72 can be released from the female input connector 98 by depressing the thumb tab 250 and engaging the detent 246 with the lip 248 once again.

Figure 5B:
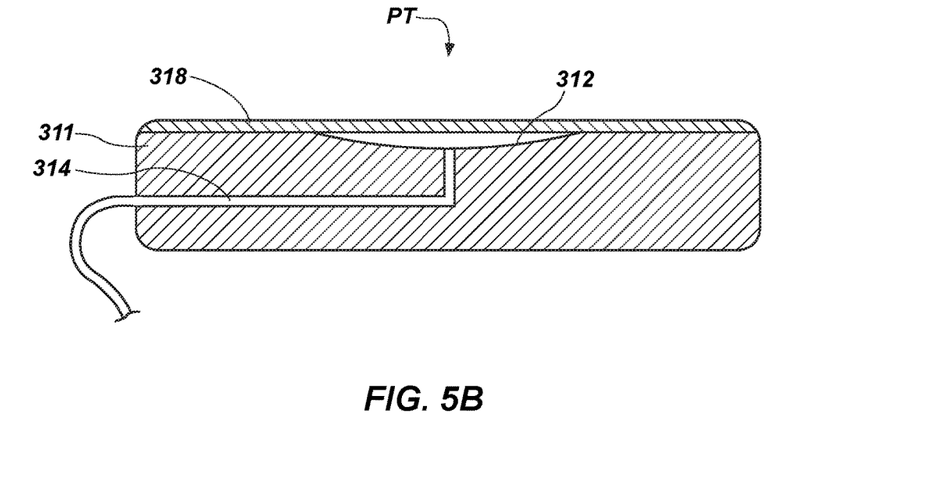
FIG. 5B is a side sectional elevation of another sensor configured for use with an embodiment of the present disclosure when employed with an output connection configured to engage the input connection of FIG. 3.

FIG. 5B depicts an embodiment of a pneumatic tocodynamometer PT as described in International PCT Publication No. WO 2012/108950, previously incorporated herein by reference. Pneumatic tocodynamometer PT may include a body 311 provided with a low profile having a shallow depression 312 in a central location of the body 311, the shallow depression 312 surrounded by a guard ring. The shallow depression 312 may be in fluid communication with an airway 314 extending through the body 311, which may be in fluid communication with a male output connector similar to the male output connector 72 for connection to the female input connector 98 of the cable 10'. Pneumatic tocodynamometer PT may be employed with a male output connector 72 configured as depicted in and described with respect to FIGS. 5 and 6, using only inner tube 130 for a connection between male output connector and pneumatic tocodynamometer PT unless an outer tube 116 is desired for mechanical and environmental protection of inner tube 130. However, as shown in broken lines in FIGS. 5 and 6, when employed with pneumatic tocodynamometer PT, male output connector incorporates an initiation element 40 as shown in broken lines, in this instance a magnetic material, to provoke proximity switch PS in the form of a reed switch, as depicted in FIGS. 3 and 6, to close when male output connector is engaged with female input connector 98 and initiation element 40 is placed a sufficiently close distance to proximity switch PS. The pneumatic tocodynamometer PT may also include a flexible membrane 318 that is stretched across the body 311 and over the shallow depression 312, to form a volume between the flexible membrane 318 and the shallow depression 312. The flexible membrane 318 may be attached to the body 311 by an adhesive, for example. When the male output connector coupled to the pneumatic tocodynamometer PT is mated with the female input connector 98 of the cable 10', air trapped between the flexible membrane 318 and the shallow depression 312, within the airway 314, and within tubing extending from the body 311 to the male output connector may define a closed interior air volume. Pressure applied to the membrane 318 may compress the trapped air, which may increase internal pressure that can be sensed by the pressure sensor 102 of the cable 10' (FIG. 5A).

As shown in FIGS. 5 and 6, the initiation element 40 may be incorporated into a body of the male output connector such that a volume of the initiation element 40 does not alter a volume of air used for charging a space between the shallow depression 12 and the flexible membrane 18 compared to a volume of air used for charging the balloon B. In some embodiments, a fluid pathway from an interior of the inner tube 130 to the internal space 226 may be directed around the initiation element 40, such as through one or more lumens formed in a body of the male output connector 72, if the initiation element 40 would otherwise preclude fluid communication between the inner tube 130 and the internal space 226. The presence of the initiation element 40 may trigger the circuit 150 (FIG. 5A) to process a signal from the pressure sensor 102 differently than if the initiation element 40 is not present.

Figure 7:
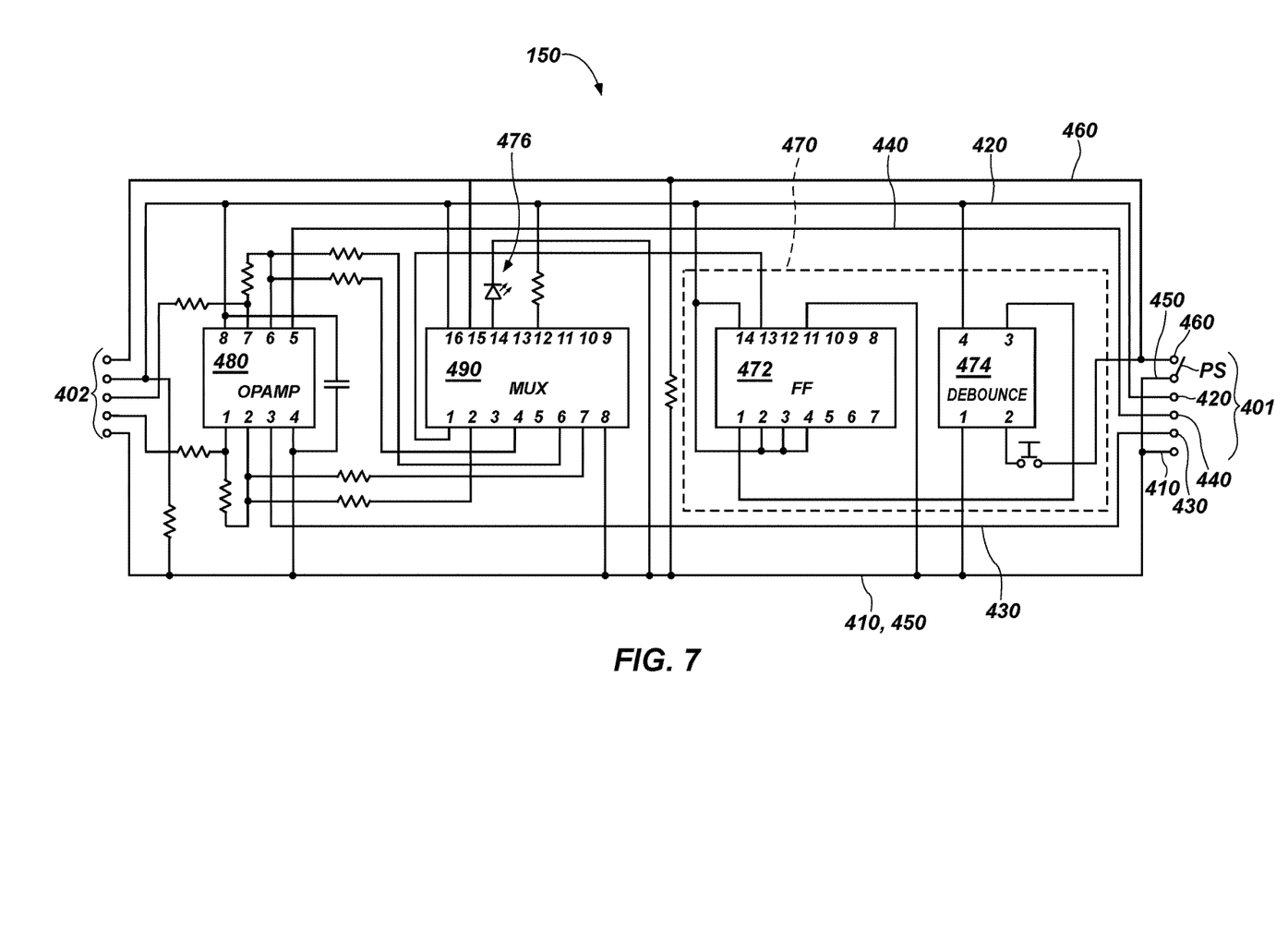
FIG. 7 is a schematic of a circuit employed with the cable embodiment of FIG. 3.

FIG. 7 schematically depicts a circuit 150 suitable for use in an embodiment of the present disclosure and, more specifically, with the embodiment of FIGS. 3, 4A, and 4B. As noted above with reference to FIG. 3, the circuit 150 may be operatively coupled to the pressure sensor 102 and configured to process a signal from the pressure sensor 102 for transmission to a monitor through the cable 10'. The circuit 150 may be configured to accept different outputs of at least two different sensors having a common output connection configuration at inputs 401 of the circuit 150. The circuit 150 may also be configured to provide a signal at outputs 402 of the circuit 150, such as for use by a monitor, corresponding to the accepted sensor output. For example, a signal from a first sensor may be received at the circuit inputs 401 and provided at the circuit outputs 402 with a unity gain, while a signal from a second, different sensor may be received at the circuit inputs 401 and provided at the circuit outputs 402 with a predetermined gain greater than one. To process the signals from the at least two different sensors, the circuit 150 may include electrical signal processing units, such as a controller 470, an amplifier 480, and a multiplexer 490.

In some embodiments, the inputs 401 for the circuit 150 may include a ground line 410, a power line 420, a first signal line 430, a second signal line 440, a first switch line 450, and a second switch line 460. The first signal line 430 may receive a sensor signal from the pressure sensor 102 (FIG. 3). The second signal line 440 may receive a reference signal. In addition, the proximity switch PS may be coupled to the first and second switch lines 450, 460, such that an electrical pathway (e.g., short) may be formed between the first and second switch lines 450, 460 by the proximity switch PS responsive to an initiation element 40 (FIG. 6) being positioned proximate the proximity switch PS. The second switch line 460 may be electrically connected to the multiplexer 490. Furthermore, the first switch line 450 may be electrically connected to the ground line 410, such that closing the proximity switch PS to connect the first switch line 450 to the second switch line 460 may cause the second switch line 460 to drop from an initial, relatively high voltage to a relatively low voltage of the ground line 410. In addition, a voltage to the input of the multiplexer 490 from the second switch line 460 (shown at pin 15 of the multiplexer 490 in FIG. 7) may also drop to the relatively low voltage when the proximity switch PS is closed. The dropping of the voltage of the second switch line 460 may trigger the multiplexer 490 to cause the amplifier 480 to apply a predetermined gain to the signal of the first signal line 430. The circuit 150 may be configured to cause the amplifier 480 to amplify a signal at a gain greater than one only when the proximity switch PS is closed.

By way of non-limiting example, the controller 470 may include a flip-flop unit 472 (e.g., a J-K flip-flop unit) and a debouncer unit 474 configured to control a light-emitting diode (LED) indicator light 476. The LED indicator light 476 may produce light when the proximity switch PS is closed responsive to an initiation element 40. The LED indicator light 476 may indicate the use of one of at least two different sensors, such as whether an IUPC or a pneumatic tocodynamometer PT is being used. The LED indicator light 476 may also provide a visual verification that the circuit 150 is set to properly process an electrical signal, depending on the particular sensor being used. In other embodiments, the controller 470 may be a micro-controller configured (e.g., programmed) to perform the functions of the flip-flop unit 472 and the debouncer unit 474 described above.

If the proximity switch PS is not closed and the second switch line 460 has a relatively high voltage, then electrical signals of the first and second signal lines 430, 440 may be processed by the amplifier 480 by outputting the electrical signals with a unity gain. In other words, the electrical signals may not be amplified by the amplifier 480 if the proximity switch PS is not closed. However, if the proximity switch PS is closed and the second switch line 460 has a relatively low voltage, then the multiplexer 490 may cause the electrical signals of the first and second signal lines 430, 440 to be amplified by the amplifier 480 with a predetermined gain. By way of example and not limitation, the predetermined gain may be between about 2.0 and about 4.0, such as between about 2.5 and about 3.5. Accordingly, referring to FIG. 7 in conjunction with FIG. 6, if a male output connector including an initiation element 40 (e.g., of a pneumatic tocodynamometer PT) is coupled to the female input connector 98, then the proximity switch PS will close and cause the circuit 150 to process a signal from the pressure sensor 102 with a predetermined gain. In addition, the LED indicator light 476 may turn on to indicate that a gain is being applied to the signal. However, if a male output connector 72 lacking an initiation element 40 (e.g., of an IUPC) is coupled to the female input connector 98, then the proximity switch PS (FIG. 3) will remain open and the circuit 150 may apply no gain to a signal from the pressure sensor 102. Thus, an output signal from the circuit 150 may be processed (or not processed, if appropriate) to provide an input for a monitor having an appropriate characteristic (e.g., voltage).

Although the proximity switch PS has been described above as being normally open ("n.o."), in other embodiments the proximity switch PS or other switching device may be normally closed ("n.c."). One of ordinary skill in the art will be capable of modifying the circuit 150 to operate with a normally closed proximity switch PS or other switching device.

Figure 8:
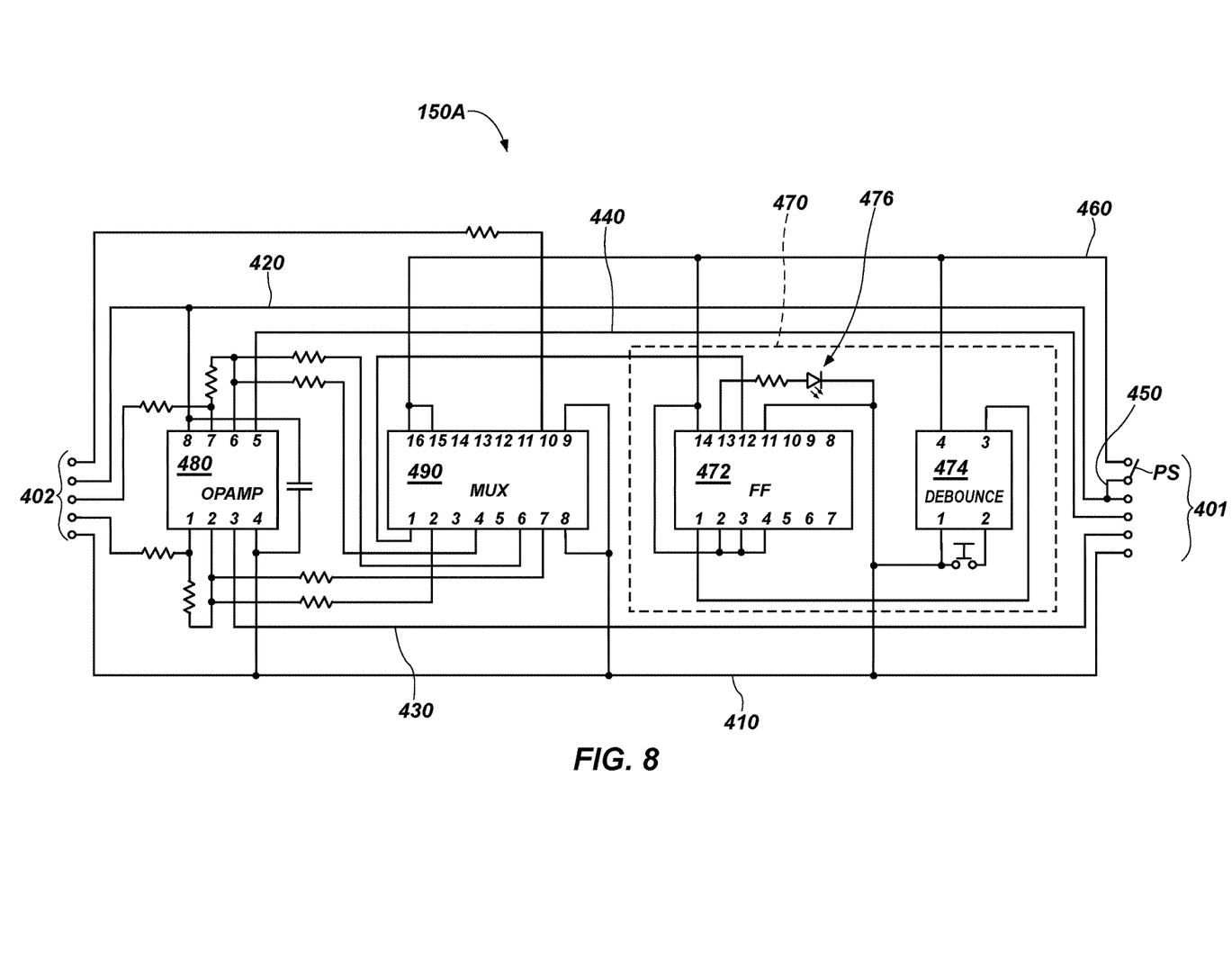
FIG. 8 is a schematic of another circuit that may be employed with the cable embodiment of FIG. 3.

Although a specific embodiment of the circuit 150 has been shown, the present disclosure is not so limited. For example, as shown in FIG. 8, another circuit 150A may be configured to perform the same or similar functions as the circuit 150 of FIG. 7, by connecting the first switch line 450 to the power line 420 rather than to the ground line 410. In such an embodiment, the second switch line 460 may be connected to the multiplexer 490 and to the controller 470. Accordingly, when the proximity switch PS closes and the first and second switch lines 450, 460 are electrically connected, power may be provided to the multiplexer 490 and to the controller 470, and the multiplexer 490 may be configured to cause the amplifier 480 to amplify a signal at a gain greater than one only when the multiplexer 490 receives power. Thus, the present disclosure also includes other embodiments of the circuit 150 that enable a variable gain to be applied to a signal depending on whether a proximity switch PS or other switching element is closed.

Although embodiments of the present disclosure have been described above as being used to process electrical signals from two different sensors, the present disclosure is not so limited. For example, a switching element similar to those described above with reference to FIGS. 2A through 2C may be modified to switch between three or more states corresponding to three or more different sensors. The circuit 150 may also be modified to apply three different gains to signals corresponding to the three or more different sensors. One of ordinary skill in the art will be able to duplicate and modify the components of the embodiments described above, as necessary, to process electrical signals from three or more different sensors.

While particular embodiments of the present disclosure have been shown and described, numerous variations and alternate embodiments, as well as different combinations of features from the various embodiments illustrated and described herein, will occur to those of ordinary skill in the art and are encompassed within the present disclosure. Accordingly, the scope of the present disclosure is limited only by the appended claims and their legal equivalents.

What is claimed is:

1. A cable assembly, comprising:
   a circuit;
   a switching element comprising a cable sensor; and
   an input connection comprising a pressure transducer and an input receptacle that is configured to interchangeably accept and engage output connectors of an intrauterine pressure catheter and of a pneumatic tocodynamometer;
   wherein the circuit of the cable assembly is configured to accept different sensor outputs of the intrauterine pressure catheter and the pneumatic tocodynamometer having a common output connection configuration and to provide an electrical signal corresponding to the accepted sensor output; and
   wherein the switching element is configured to, responsive to the cable sensor sensing a connection signal from the intrauterine pressure catheter or the pneumatic tocodynamometer, selectively enable the circuit to process the accepted sensor output of at least one of the intrauterine pressure catheter or the pneumatic tocodynamometer prior to providing the electrical signal corresponding thereto.

2. The cable assembly of claim 1, wherein the switching element is selected from the group consisting of a proximity switch, a reed switch, a Hall effect sensor, two spaced contacts, a spring-based contact switch, and an optical emitter/receiver switch.

3. The cable assembly of claim 1, wherein the circuit comprises an amplifier configured to amplify the output of at least one of the intrauterine pressure catheter or the pneumatic tocodynamometer.

4. The cable assembly of claim 3, wherein the circuit is configured to cause the amplifier to amplify the output of one of the intrauterine pressure catheter or the pneumatic tocodynamometer at a predetermined gain of between about 2.0 and about 4.0.

5. The cable assembly of claim 1, further comprising an indicator light operatively coupled to the circuit and configured to indicate whether an output connection of one of the intrauterine pressure catheter or the pneumatic tocodynamometer is engaged with the input connection.

6. A uterine contraction sensor, comprising:
a sensor element selected from the group consisting of an intrauterine pressure catheter and a pneumatic tocodynamometer;
an output connection in fluid pressure communication with the sensor element; and
an initiation element proximate the output connection, and structured and configured to provide an indication to a switching element associated with an input connection of a cable comprising a circuit to cause the circuit to change a mode of operation of the switching element responsive to engagement of the output connection with the input connection to enable the circuit of the cable to process an electrical signal corresponding to an output of the sensor element and to provide a processed electrical signal corresponding to the output of the sensor element.

7. The uterine contraction sensor of claim 6, wherein the initiation element is selected from the group consisting of a magnet, a metal, a conductive material, a key element, a light conductive material, and a reflective element.

8. The uterine contraction sensor of claim 6, herein the initiation element is incorporated into a body of the output connection to enable a volume of air for charging the sensor to be substantially the same as a volume of air for charging a sensor lacking the initiation element.

9. A uterine contraction monitoring system comprising:
a uterine contraction monitor;
at least two different sensors comprising an intrauterine pressure catheter and a pneumatic tocodynamometer, one of the at least two different sensors comprising an initiation element, another of the at least two different sensors lacking an initiation element; and
a cable configured for operative connection to the uterine contraction monitor and for interchangeable connection to the at least two different sensors, the cable including:
a circuit electrically coupled to a pressure transducer;
an input connection comprising the pressure transducer, the input connection for interchangeably engaging a respective sensor output connection of the at least two different sensors and for providing a pressure signal from the at least two different sensors to the pressure transducer, the input connection configured to provide differing sensor outputs acceptable by the circuit;
a cable output connection for respectively providing an electrical signal output to the monitor from the respective at least two different sensors; and
a switching element associated with the input connection, the switching element configured to, responsive to a connection signal from the initiation element, selectively enable the circuit of the cable to process a sensor output of the one of the at least two different sensors that comprises the initiation element and to provide the electrical signal output corresponding to the acceptable sensor output to the uterine contraction monitor.

10. The uterine contraction monitoring system of claim 9, wherein the circuit comprises an amplifier configured to selectively amplify the output of the at least one of the at least two different sensors.

11. A method of using uterine contraction sensors, the method comprising:
connecting a first uterine contraction sensor configured to provide a first sensor output to an input receptacle of a cable operably coupled to a monitor;
providing the first sensor output to the cable;
converting the first sensor output to corresponding electrical signals usable by the monitor and transmitting the electrical signals corresponding to the first sensor output through the cable to the monitor;
disconnecting the sensor from the input receptacle of the cable;
connecting to the same input receptacle of the cable a second, different uterine contraction sensor comprising an initiation element and being configured to provide a second, different sensor output from the first sensor output;
providing the second, different uterine contraction sensor output to the cable;
using the initiation element of the second, different uterine contraction sensor to cause a switching element associated with the input receptacle to change a mode of operation of the switching element responsive to engagement of the second, different uterine contraction sensor with the input receptacle and to enable processing of the second, different sensor output;
converting the second, different sensor output to corresponding different electrical signals;
processing the different electrical signals into a form usable by the monitor; and
transmitting the processed different electrical signals to the monitor.

12. The method of claim 11, wherein connecting the first uterine contraction sensor to the input receptacle of the cable comprises connecting an intrauterine pressure catheter to the input receptacle of the cable, and wherein connecting to the same input receptacle of the cable the second, different uterine contraction sensor comprises connecting a pneumatic tocodynamometer to the input receptacle of the cable.

13. The method of claim 11, wherein transmitting the electrical signals comprises amplifying the electrical signals with a unity gain and wherein processing the different electrical signals comprises amplifying the different electrical signals with a greater than unity gain.

14. The method of claim 11, wherein connecting to the same input receptacle of the cable the second, different uterine contraction sensor comprises activating a proximity switch of the cable.

15. The method of claim 11, wherein converting the first sensor output to corresponding electrical signals comprises converting a pressure output to corresponding electrical signals using a pressure transducer associated with the input receptacle of the cable.

* * * * *

UNITED STATES PATENT AND TRADEMARK OFFICE
CERTIFICATE OF CORRECTION

PATENT NO.       : 9,734,706 B2
APPLICATION NO.  : 13/830239
DATED            : August 15, 2017
INVENTOR(S)      : Brandon D. Moon, Kristian J. Olsen and Jeremy C. Horton It is certified that error appears in the above-identified patent and that said Letters Patent is hereby corrected as shown below:

In the Claims

Column 13,   Line 36,   Claim 8,   change "claim 6, herein" to --claim 6, wherein--

Signed and Sealed this
Twenty-seventh Day of February, 2018

Andrei Iancu
*Director of the United States Patent and Trademark Office*